United States Patent [19]
Buckwalter et al.

[11] Patent Number: 5,973,190
[45] Date of Patent: Oct. 26, 1999

[54] PROCESS AND INTERMEDIATE COMPOUNDS FOR THE PREPARATION OF PESTICIDAL FLUOROOLEFIN COMPOUNDS

[75] Inventors: Brian Lee Buckwalter, Yardley; Timothy Claude Barden, Holland, both of Pa.

[73] Assignee: American Cyanamid Company, Madison, N.J.

[21] Appl. No.: 09/099,101

[22] Filed: Jun. 18, 1998

Related U.S. Application Data

[60] Provisional application No. 60/050,166, Jun. 19, 1997.

[51] Int. Cl.$^6$ .......................... C07C 69/76; C07C 19/08
[52] U.S. Cl. ............................. 560/51; 560/53; 560/55; 560/56; 560/59; 562/459; 562/462; 562/463; 570/128
[58] Field of Search .................. 560/51, 53, 55, 560/59; 562/459, 462, 463; 570/128

[56] References Cited

FOREIGN PATENT DOCUMENTS

| 2288803 | 4/1995 | United Kingdom . |
| WO 97/16067 | 5/1990 | WIPO . |
| WO 94/06741 | 3/1994 | WIPO . |

OTHER PUBLICATIONS

Mills, F.D.; Mills, G.D.; Brown, R.T., *Journal of Agricultural and Food Chemistry,* 1989, 37, 501–507.

*Primary Examiner*—Paul J. Killos
*Attorney, Agent, or Firm*—Joseph M. Mazzarese

[57] ABSTRACT

The present invention provides a process for the preparation of pesticidal fluoroolefin compounds having the structural formula I

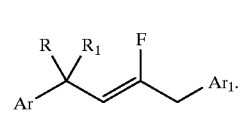

(I)

The present invention also provides intermediate compounds which are utilized in the process of this invention.

23 Claims, No Drawings

PROCESS AND INTERMEDIATE COMPOUNDS FOR THE PREPARATION OF PESTICIDAL FLUOROOLEFIN COMPOUNDS

This application claims benefit of Provisional Application No. 60/050,166, filed Jun. 19, 1997.

BACKGROUND OF THE INVENTION

Fluoroolefin compounds which are useful as pesticidal agents are described in WO 94/06741 and GB 2,288,803-A. Those patent applications also describe processes for the preparation of fluoroolefin compounds. However, those processes are not entirely satisfactory because they require the use of Grignard reagents, alkali metal compounds and transition metal catalysts. In addition, those processes produce the fluoroolefin compounds in relatively low yields.

It is, therefore, an object of the present invention to provide a novel, effective and efficient process for the preparation of pesticidal fluoroolefin compounds which does not require the use of Grignard reagents, alkali metal compounds and transition metal catalysts.

It is also an object of the present invention to provide intermediate compounds which are useful for the preparation of pesticidal fluoroolefin compounds.

Other objects and advantages of the present invention will be apparent to those skilled in the art from the description below and the appended claims.

SUMMARY OF THE INVENTION

The present comprises a process for the preparation of a pesticidal fluoroolefin compound having the structural formula I

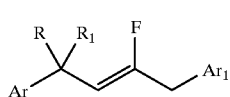

(I)

wherein

R is hydrogen or $C_1$–$C_4$alkyl, and $R_1$ is $C_1$–$C_4$alkyl, $C_1$–$C_4$haloalkyl or cyclopropyl, or R and $R_1$ are taken together with the carbon atom to which they are attached to form a cyclopropyl group;

Ar is phenyl optionally substituted with up to three groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups, or 1- or 2-naphthyl optionally substituted with up to three groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups;

$Ar_1$ is phenoxyphenyl optionally substituted with up to five groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups, biphenyl optionally substituted with up to five groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups, benzylphenyl optionally substituted with up to five groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups, or benzoylphenyl optionally substituted with up to five groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups; and the configuration of the groups $ArCRR_1$— and —$CH_2Ar_1$ about the double bond is predominantly mutually trans, which process comprises a) fluorinating a 4-aryl-3-oxo-2-(substituted benzyl)butanoate compound having the structural formula II

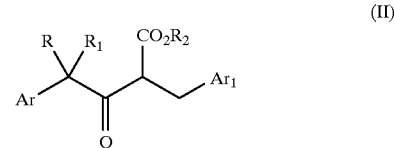

(II)

wherein $R_2$ is $C_1$–$C_6$alkyl and Ar, $Ar_1$, R and $R_1$ are as described above in the presence of a first base to form a 4-aryl-2-fluoro-3-oxo-2-(substituted benzyl)butanoate compound having the structural formula III

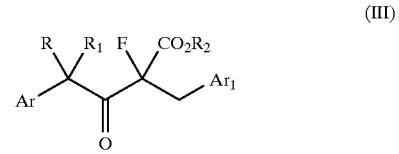

(III)

wherein Ar, $Ar_1$, R, $R_1$ and $R_2$ are as described above;

b) reducing the formula III compound to form a 4-aryl-2-fluoro-3-hydroxy-2-(substituted benzyl)butanoate compound having the structural formula IV

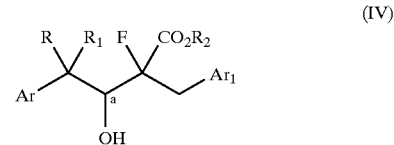

(IV)

wherein Ar, $Ar_1$, R, $R_1$ and $R_2$ are as described above and the configuration of the groups $ArCRR_1CH(OH)$— and —CF($CO_2R_2$)$CH_2Ar_1$ attached to the bond labelled "a" is predominantly R,S or S,R or a mixture thereof;

c) saponifying the formula IV compound to form a 4-aryl-2-fluoro-3-hydroxy-2-(substituted benzyl) butanoic acid compound having the structural formula V

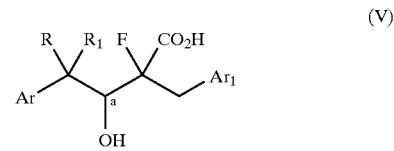

(V)

wherein Ar, $Ar_1$, R and $R_1$ are as described above and the configuration of the groups $ArCRR_1CH(OH)$— and —CF($CO_2H$)$CH_2Ar_1$ attached to the bond labelled "a" is predominantly R,S or S,R or a mixture thereof; and d) reacting the formula V compound with a sulfonyl halide compound and a second base.

The present invention further comprises the intermediate compounds of formulas III, IV and V.

DETAILED DESCRIPTION OF THE INVENTION

A preferred embodiment of the present invention comprises a) fluorinating the formula II compound with at least about one molar equivalent of a fluorinating agent in the presence of at least about one molar equivalent of a first base, preferably in a temperature range of about —15° C. to 100° C., in the presence of a first solvent to form a 4-aryl-2-fluoro-3-oxo-2-(substituted benzyl)-butanoate of formula III;

b) reducing the formula III compound with at least about one molar equivalent of a reducing agent, preferably in a temperature range of about —50° C. to 80° C., in the presence of a second solvent to form a 4-aryl-2-fluoro-3-hydroxy-2-(substituted benzyl)butanoate of formula IV;

c) saponifying the formula IV compound by reaction with at least about one molar equivalent of a first base, followed by at least about one molar equivalent of an acid, preferably in a temperature range of about −15° C. to 80° C. and in the presence of a third solvent, to form a 4-aryl-2-fluoro-3-hydroxy-2-(substituted benzyl) butanoic acid of formula V; and d) reacting the formula V compound with at least about one molar equivalent of a sulfonyl halide compound and at least about one molar equivalent of a second base, preferably in a temperature range of about 0° C. to 130° C., optionally in the presence of a fourth solvent.

The present invention also includes the 4-aryl-2-fluoro-3-oxo-2-(substituted benzyl)butanoate compounds, the 4-aryl-2-fluoro-3-hydroxy-2-(substituted benzyl)-butanoate compounds, and the 4-aryl-2-fluoro-3-hydroxy-2-(substituted benzyl)butanoic acid compounds which are utilized in the process of this invention. Those compounds are represented by the structural formulas III, IV and V, respectively,

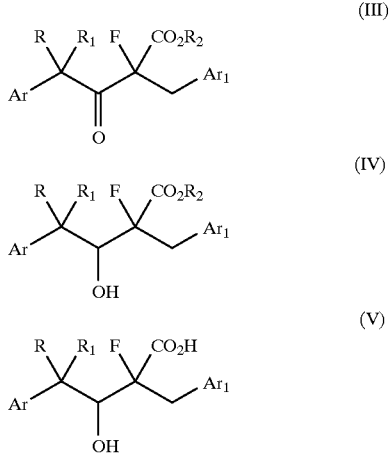

wherein

R is hydrogen or $C_1$–$C_4$alkyl, and $R_1$ is $C_1$–$C_4$alkyl, $C_1$–$C_4$haloalkyl or cyclopropyl, or R and $R_1$ are taken together with the carbon atom to which they are attached to form a cyclopropyl group;

Ar is phenyl optionally substituted with up to three groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups, or 1- or 2-naphthyl optionally substituted with up to three groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups;

$Ar_1$ is phenoxyphenyl optionally substituted with up to five groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups, biphenyl optionally substituted with up to five groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups, benzylphenyl optionally substituted with up to five groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups, or benzoylphenyl optionally substituted with up to five groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups; and $R_2$ is $C_1$–$C_6$alkyl; and the optical isomers and diastereomers thereof.

Exemplary of halogen hereinabove are fluorine, chlorine, bromine and iodine. The terms "$C_1$–$C_4$haloalkyl" and "$C_1$–$C_4$haloalkoxy" are defined as a $C_1$–$C_4$alkyl group and a $C_1$–$C_4$alkoxy group substituted with one or more halogen atoms, respectively.

The product formula I compounds may be isolated by diluting the reaction mixture with water and extracting the product with a suitable extraction solvent. In the isolation procedure, conventional extraction solvents such as ether, ethyl acetate, toluene, methylene chloride and the like may be utilized.

Advantageously, the unique process of this invention provides pesticidal fluoroolefin compounds in relatively high yields. In addition, the process of this invention does not utilize the uneconomical reagents required by the art processes.

Fluorinating agents suitable for use in this invention include, but are not limited to, fluorine, diethylaminosulfur trifluoride, 1-fluoro-4-hydroxy-1,4-diazoniabicyclo[2.2.2] octane bis(tetrafluoroborate), N-fluoropyridinium pyridine heptafluorodiborate, N-fluorobenzenesulfonimide, N-fluoro-3,3-dimethyl-2,3-dihydro-1,2-benzothiazol-1,1-dioxide, an N-fluoro oxathiazinone dioxide, and the like, and mixtures thereof. N-Fluoro-3,3-dimethyl-2,3-dihydro-1,2-benzothiazol-1,1-dioxide is a preferred fluorinating agent.

Reducing agents suitable for use in the present invention produce formula IV compounds wherein the configuration of the groups $ArCRR_1CH(OH)$— and —$CF(CO_2R_2)CH_2Ar_1$ is predominantly R,S or S,R or a mixture thereof. Reducing agents which may be utilized in this invention include, but are not limited to, enzymatic reduction systems, whole cell microorganisms, borohydrides such as sodium borohydride, sodium cyano borohydride, zinc borohydride and the like, substituted aluminum hydrides such as lithium tri-tert-butoxyaluminum hydride and the like, aluminum $C_1$–$C_4$alkoxide/$C_1$–$C_6$alcohol complexes such as an aluminum isopropoxide/isopropanol complex and the like, and hydrogen in the presence of a noble metal catalyst. Borohydrides are preferred reducing agents.

Bases suitable for use in the saponification step of the present invention include, but are not limited to, alkali metal carbonates such as sodium carbonate and potassium carbonate, alkaline earth metal carbonates such as calcium carbonate, alkali metal hydroxides such as sodium hydroxide and potassium hydroxide, alkaline earth metal hydroxides such as calcium hydroxide, alkali metal $C_1$–$C_6$alkoxides such as sodium ethoxide and potassium tert-butoxide, alkaline earth metal $C_1$–$C_6$alkoxides, thallium (I) carbonate, thallium(I) $C_1$–$C_6$alkoxides, and thallium(I) hydroxide, and mixtures thereof, with alkali metal hydroxides being preferred. Acids suitable for use in this invention include mineral acids such as hydrochloric acid, hydrobromic acid, sulfuric acid and the like, and strong organic acids such as trifluoroacetic acid and the like, and mixtures thereof, with mineral acids being preferred.

Sulfonyl halide compounds suitable for use in the present invention include, but are not limited to, alkylsulfonyl chlorides such as methanesulfonyl chloride and the like, and arylsulfonyl chlorides such as p-toluenesulfonyl chloride, benzenesulfonyl chloride and the like, and mixtures thereof.

First bases suitable for use in the present invention include, but are not limited to, alkali metal $C_1$–$C_6$alkoxides such as sodium ethoxide and potassium tert-butoxide, alkali metal hydrides such as sodium hydride, alkali metal hydroxides such as sodium hydroxide and potassium hydroxide, alkaline earth metal hydroxides such as calcium hydroxide, alkyl lithiums such as n-butyl-lithium and s-butyllithium, aryl lithiums such as phenyl lithium, alkaline earth metal $C_1$–$C_6$alkoxides, thallium(I) $C_1$–$C_6$alkoxides, and thallium (I) hydroxide, and mixtures thereof. Preferred first bases include alkali metal $C_1$–$C_6$alkoxides and alkali metal hydrides. Second bases suitable for use in this invention include, but are not limited to, tertiary amines such as tri($C_1$–$C_4$alkyl)amines, pyridine and substituted pyridines, with pyridine being preferred.

First solvents suitable for use in the fluorinating step of the present invention include, but are not limited to, ethers such as tetrahydrofuran, dioxane and the like, aromatic hydrocarbons such as toluene, benzene, xylenes, mesitylene and the like, halogenated aromatic hydrocarbons such as chlorobenzene, fluorobenzene and the like, and carboxylic acid amides such as N,N-dimethyl-formamide and the like, and mixtures thereof. Preferred first solvents include ethers with tetrahydrofuran being more preferred.

Second and third solvents (which may be the same or different) suitable for use in this invention include, but are not limited to, $C_1$–$C_4$alcohols such as methanol, ethanol and the like, and ethers such as tetrahydrofuran, dioxane and the like, and mixtures thereof. Preferred second and third solvents include $C_1$–$C_4$alcohols with methanol being more preferred.

Fourth solvents suitable for use in the present invention include, but are not limited to, aromatic hydrocarbons such as toluene, benzene, xylenes, mesitylene and the like, halogenated aromatic hydrocarbons such as chlorobenzene, fluorobenzene and the like, ethers such as tetrahydrofuran, dioxane and the like, carboxylic acid amides such as N,N-dimethyl-formamide and the like, halogenated aliphatic hydrocarbons such as chloroform, carbon tetrachloride and the like, and acetonitrile, and mixtures thereof.

The present invention also includes the novel compounds represented by formulae II, III, IV, and V, wherein Ar, $Ar_1$, R, $R_1$ and $R_2$ are as described hereinabove, provided that in compounds of formula II R is other than hydrogen.

Starting 4-aryl-3-oxobutanoate compounds of formula II may be prepared, as illustrated in Flow Diagram I, by reacting a 4-aryl-3-oxobutanoate of formula VI with a base and a substituted benzyl halide of formula VII.

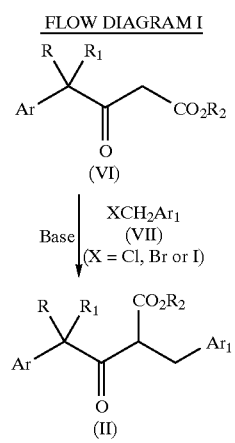

FLOW DIAGRAM I

Preferred formula I fluoroolefin compounds which may be prepared by the process of this invention are those wherein R is hydrogen and $R_1$ is isopropyl or cyclopropyl, or R and $R_1$ are methyl, or R and $R_1$ are taken together with the carbon atom to which they are attached to form a cyclopropyl group;

Ar is phenyl optionally substituted with up to three groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups; and $Ar_1$ is 3-phenoxyphenyl optionally substituted with up to five groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups, 3-biphenyl optionally substituted with up to five groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups, 3-benzylphenyl optionally substituted with up to five groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups, or 3-benzoylphenyl optionally substituted with up to five groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups.

The process of the present invention is particularly useful for the preparation of pesticidal fluoroolefins of formula I wherein R is hydrogen and $R_1$ is isopropyl or cyclopropyl, or R and $R_1$ are methyl, or R and $R_1$ are taken together with the carbon atom to which they are attached to form a cyclopropyl group;

Ar is 4-chlorophenyl, 4-fluorophenyl, 4-(trifluoromethoxy)phenyl or 4-ethoxyphenyl; and $Ar_1$ is 4-fluoro-3-phenoxyphenyl or 3-phenoxyphenyl.

Preferred starting formula II compounds of the present invention are those wherein $R_2$ is $C_1$–$C_4$alkyl.

In order to facilitate a further understanding of the invention, the following examples are presented primarily for the purpose of illustrating more specific details thereof. The scope of the invention should not be deemed limited by the examples, but encompasses all of the subject matter defined in the claims.

EXAMPLE 1

Preparation of Ethyl 1-(p-chlorophenyl)-α-fluoro-β-oxo-α-(m-phenoxybenzyl)cyclopropanepropionate

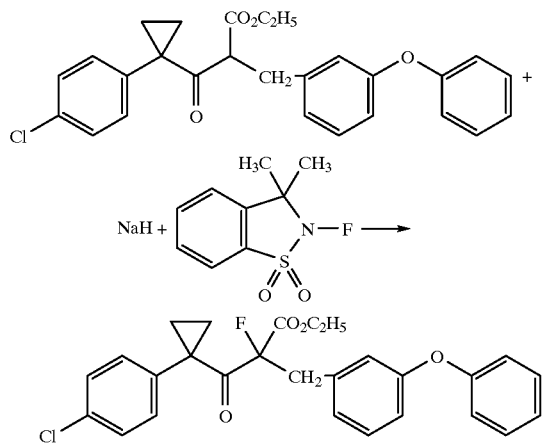

A 60% sodium hydride dispersion in oil (0.17 g, 4.3 mmol) is washed with hexanes, dried and dispersed in tetrahydrofuran. The resultant mixture is cooled with an ice-water bath, treated with a solution of ethyl 1-(p-chlorophenyl)-β-oxo-α-(m-phenoxybenzyl) cyclopropanepropionate (1.72 g 3.84 mmol) in tetrahydrofuran, stirred at 0° C. for 4 hours, treated with a solution of N-fluoro-3,3-dimethyl-2,3-dihydro-1,2-benzothiazol-1,1-dioxide (1.10 g, 5.12 mmol) in tetrahydrofuran, stirred at 0° C. for 90 minutes, stirred at room temperature for one hour, cooled in an ice-water bath, quenched with 10 mL of brine, and diluted with ethyl acetate and water. The organic phase is separated, washed sequentially with water and brine, dried over anhydrous sodium sulfate and concentrated in vacuo to obtain a residue. Chromatography of the residue using silica gel and a 19:1 hexanes/ethyl acetate solution gives the title product as a colorless oil (1.25 g, 70%) which is identified by NMR spectral analysis.

EXAMPLE 2

Preparation of Ethyl 1-(p-chlorophenyl)-α-fluoro-β-hydroxy-α-(m-phenoxybenzyl) cyclopropanepropionate, 9:1 [R,S and S,R] to [R,R and S,S] ratio

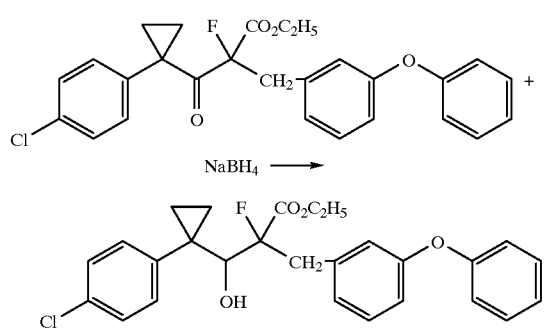

Sodium borohydride (20 mg, 0.53 mmol) is added to a solution of ethyl 1-(p-chlorophenyl)-α-fluoro-β-oxo-α-(m-phenoxybenzyl)cyclopropanepropionate (214 mg, 0.46 mmol) in methanol at 0° C. The reaction mixture is stirred at 0° C. for 20 minutes, treated with water (2 mL), and concentrated in vacuo to obtain a residue. A solution of the residue in ethyl acetate is washed sequentially with water and brine, dried over anhydrous sodium sulfate, and concentrated in vacuo to give the title product as a colorless gum (224 mg, 100%) which is found to have a 9:1 [R,S and S,R] to [R,R and S,S] ratio by NMR spectral analyses.

EXAMPLE 3

Preparation of 1-(p-chlorophenyl)-α-fluoro-β-hydroxy-α-(m-phenoxybenzyl) cyclopropanepropionic acid, 9:1 [R,S and S,R] to [R,R and S,S] ratio

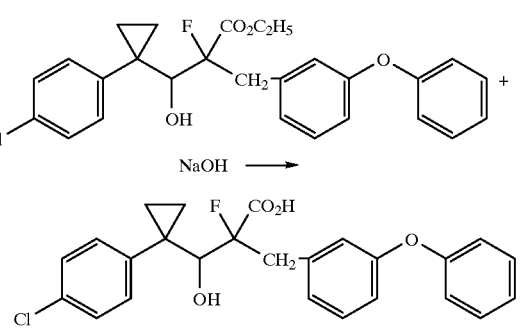

Sodium hydroxide solution (3 mL of a 1 M solution) is added to a solution of ethyl 1-(p-chlorophenyl)-α-fluoro-β-hydroxy-α-(m-phenoxybenzyl) cyclopropanepropionate having a 9:1 [R,S and S,R] to [R,R and S,S] ratio (224 mg, 0.48 mmol) in methanol at 0° C. The reaction mixture is stirred at room temperature overnight, acidified to pH 1 with concentrated hydrochloric acid, and concentrated in vacuo to obtain a residue. A solution of the residue in ethyl acetate is washed sequentially with water and brine, dried over anhydrous sodium sulfate, concentrated in vacuo, diluted with diethyl ether and hexanes, and concentrated in vacuo to give the title product as a white foam (210 mg, 100%) which is identified by NMR spectral analysis.

EXAMPLE 4

Preparation of 1-(p-Chlorophenyl)-1-[2-fluoro-3-(m-phenoxyphenyl)propenyl]cyclopropane, (9:1) Z to E ratio

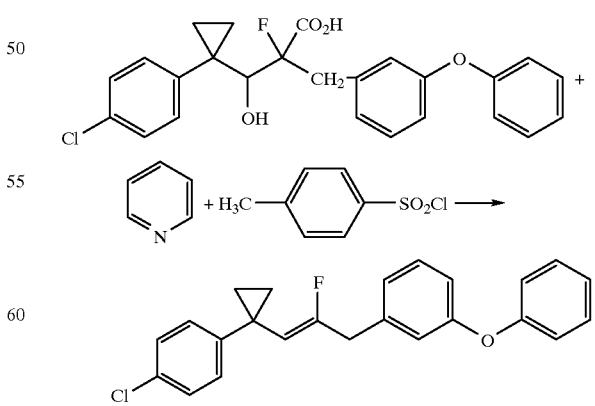

p-Toluenesulfonyl chloride (19.07 mg, 0.10 mmol) is added to a solution of 1-(p-chlorophenyl)-α-fluoro-β- hydroxy-α-(m-phenoxybenzyl)cyclopropanepropionic acid having a 9:1 [R,S and S,R] to [R,R and S,S] ratio (20 mg, 0.05 mmol) in pyridine (2 mL). The reaction mixture is heated to 60° C. and poured into water. The aqueous mixture is extracted with diethyl ether. The organic extracts are combined, washed sequentially with 2 N hydrochloric acid, water, 10% sodium hydrogen carbonate solution and brine, dried over anhydrous sodium sulfate, and concentrated in vacuo to give the title product as a colorless oil (18 mg, 100%) which is found to have a 9:1 Z to E ratio by NMR spectral analyses.

EXAMPLE 5

Preparation of Ethyl 1-(p-chlorophenyl)-β-hydroxy-cyclopropanepropionate

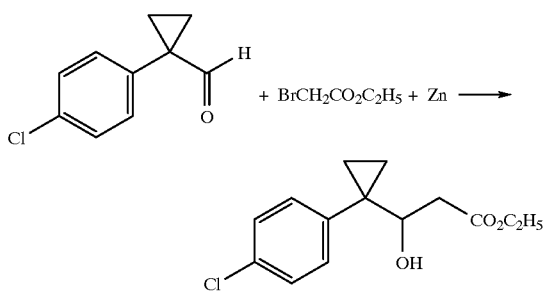

A mixture of zinc dust (4.0 g, 61.2 mmol), ethyl bromoacetate (6.5 mL, 58.3 mmol) and 1-(p-chlorophenyl)-cyclopropanecarboxaldehyde (10.0 g, 55.4 mmol) in toluene is stirred at 70° C. for 45 minutes, cooled with an ice-water bath, treated with 100 mL of 10% sulfuric acid, stirred at room temperature for one hour, and diluted with ethyl acetate. The organic phase is separated, washed sequentially with 10% sulfuric acid, water, 10% sodium hydrogen carbonate solution and brine, dried over anhydrous sodium sulfate, and concentrated in vacuo to obtain an oil. Chromatography of the oil using silica gel and a 9:1 to 7:3 hexanes/ethyl acetate gradient gives the title product as a colorless oil (11.3 g, 76%) which is identified by NMR spectral analyses.

EXAMPLE 6

Preparation of Ethyl 1-(p-chlorophenyl)-β-oxo-cyclopropanepropionate

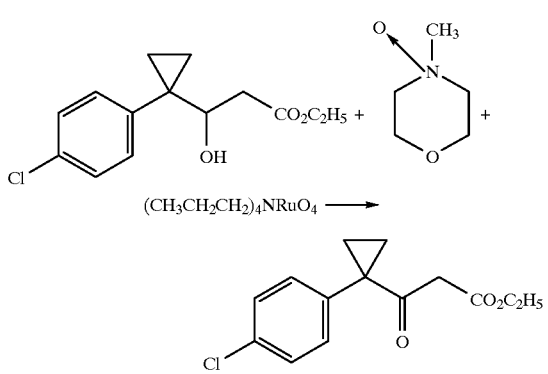

A solution of ethyl 1-(p-chlorophenyl)-β-hydroxy-cyclopropanepropionate (7.9 g, 29.4 mmol) and 4-methyl-morpholine N-oxide (14.0 g, 120 mmol) in acetonitrile containing 30 4 Å molecular sieves is stirred at room temperature for 20 minutes, treated with tetrapropylammonium perruthenate (0.8 g, 2.3 mmol), stirred for two hours while maintaining the reaction mixture temperature at room temperature with an ice-water bath, diluted with diethyl ether, filtered through diatomaceous earth, and concentrated in vacuo to obtain a residue. A solution of the residue in diethyl ether is washed sequentially with water, 5% sulfuric acid, water and brine, dried over anhydrous sodium sulfate, and concentrated in vacuo to obtain a dark oil. Chromatography of the oil using silica gel and a 1:19 to 3:17 ethyl acetate/hexanes gradient gives the title product as a pale yellow oil (4.3 g, 55%) which is identified by NMR spectral analyses.

EXAMPLE 7

Preparation of Ethyl 1-(p-chlorophenyl)-β-oxo-α-(m-phenoxybenzyl)cyclopropanepropionate

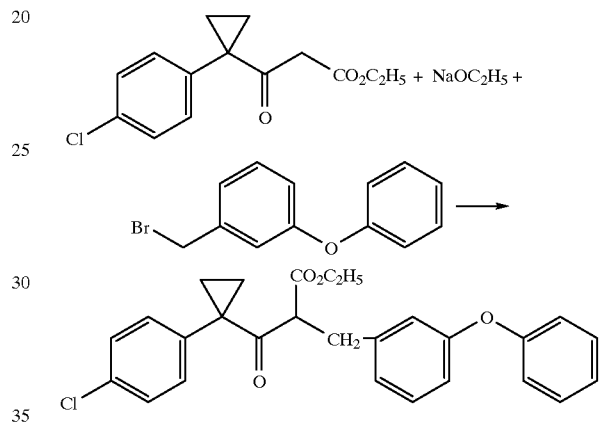

A mixture of sodium (0.31 g, 13.5 mmol) in ethanol (90 mL) is stirred at room temperature until the sodium dissolves. The resultant solution is heated to 70° C., treated dropwise with a solution of ethyl 1-(p-chlorophenyl)-β-oxocyclopropanepropionate (3.4 g, 12.8 mmol) in ethanol, stirred at 70° C. for one hour, treated dropwise with a solution of α-bromo-m-tolyl phenyl ether (4.0 g, 15.2 mmol) in ethanol, stirred at reflux overnight, stirred at room temperature for two days, and concentrated in vacuo to obtain a residue. A solution of the residue in ethyl acetate is washed sequentially with water, 10% sodium hydrogen carbonate solution and brine, dried over anhydrous sodium sulfate, and concentrated in vacuo to obtain an oil. Chromatography of the oil using silica gel and a 19:1 hexanes/ethyl acetate solution gives the title product as a colorless oil (5.24 g, 92%) which is identified by NMR spectral analysis.

We claim:
1. A process for the preparation of a fluoroolefin compound having the structural formula I

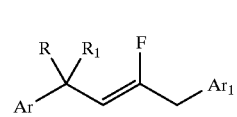

(I)

wherein
R is hydrogen or $C_1$–$C_4$alkyl, and
$R_1$ is $C_1$–$C_4$alkyl, $C_1$–$C_4$haloalkyl or cyclopropyl, or R and $R_1$ are taken together with the carbon atom to which they are attached to form a cyclopropyl group;

Ar is phenyl optionally substituted with up to three groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups, or 1- or 2-naphthyl optionally substituted with up to three groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups;

$Ar_1$ is phenoxyphenyl optionally substituted with up to five groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups, biphenyl optionally substituted with up to five groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups, benzylphenyl optionally substituted with up to five groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups, or benzoylphenyl optionally substituted with up to five groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups; and the configuration of the groups $ArCRR_1$— and —$CH_2Ar_1$ about the double bond is predominantly mutually trans, which process comprises a) fluorinating a 4-aryl-3-oxo-2-(substituted benzyl) butanoate compound having the structural formula II

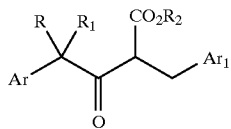

(II)

wherein $R_2$ is $C_1$–$C_6$alkyl and Ar, $Ar_1$, R and $R_1$ are as described above in the presence of a first base to form a 4-aryl-2-fluoro-3-oxo-2-(substituted benzyl)butanoate compound having the structural formula III

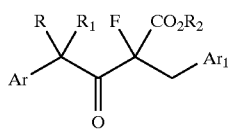

(III)

wherein Ar, $Ar_1$, R, $R_1$ and $R_2$ are as described above;

b) reducing the formula III compound to form a 4-aryl-2-fluoro-3-hydroxy-2-(substituted benzyl)butanoate compound having the structural formula IV

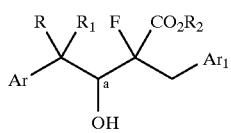

(IV)

wherein Ar, $Ar_1$, R, $R_1$ and $R_2$ are as described above and the configuration of the groups $ArCRR_1CH(OH)$— and —CF($CO_2R_2$)$CH_2Ar_1$ attached to the bond labelled "a" is predominantly R,S or S,R or a mixture thereof;

c) saponifying the formula IV compound to form a 4-aryl-2-fluoro-3-hydroxy-2-(substituted benzyl) butanoic acid compound having the structural formula V

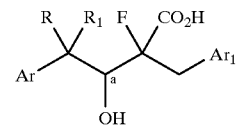

(V)

wherein Ar, $Ar_1$, R and $R_1$ are as described above and the configuration of the groups $ArCRR_1CH(OH)$— and —CF($CO_2H$)$CH_2Ar_1$ attached to the bond labelled "a" is predominantly R,S or S,R or a mixture thereof; and d) reacting the formula V compound with a sulfonyl halide compound and a second base.

2. The process according to claim 1 wherein the first base is selected from the group consisting of an alkali metal hydroxide, an alkaline earth metal hydroxide, an alkali metal $C_1$–$C_6$alkoxide, an alkaline earth metal $C_1$–$C_6$alkoxide, a thallium(I) $C_1$–$C_6$alkoxide, thallium(I) hydroxide, an alkali metal hydride, an alkyl lithium and an aryl lithium, and the second base is a tertiary amine selected from the group consisting of a tri($C_1$–$C_4$alkyl)amine, pyridine and a substituted pyridine.

3. The process according to claim 1 wherein said fluorinating step comprises reacting the formula II compound with a fluorinating agent selected from the group consisting of fluorine, diethylaminosulfur trifluoride, 1-fluoro-4-hydroxy-1,4-diazoniabicyclo[2.2.2]octane bis (tetrafluoroborate), N-fluoropyridinium pyridine heptafluorodiborate, N-fluorobenzenesulfonimide, N-fluoro-3,3-dimethyl-2,3-dihydro-1,2-benzothiazol-1,1-dioxide and an N-fluoro oxathiazinone dioxide.

4. The process according to claim 1 wherein said reducing step comprises reacting the formula III compound with a reducing agent selected from the group consisting of a borohydride, a substituted aluminum hydride, an aluminum $C_1$–$C_5$alkoxide/$C_1$–$C_6$alcohol complex and hydrogen in the presence of a noble metal catalyst.

5. The process according to claim 1 wherein said saponifying step comprises reacting the formula IV compound with a base selected from the group consisting of an alkali metal carbonate, an alkaline earth metal carbonate, an alkali metal hydroxide, an alkaline earth metal hydroxide, an alkali metal $C_1$–$C_6$alkoxide, an alkaline earth metal $C_1$–$C_6$alkoxide, thallium(I) carbonate, a thallium(I) $C_1$–$C_6$alkoxide and thallium(I) hydroxide.

6. The process according to claim 1 wherein the sulfonyl halide compound is selected from the group consisting of an alkylsulfonyl chloride and an arylsulfonyl chloride.

7. The process according to claim 1 wherein

R is hydrogen and $R_1$ is isopropyl or cyclopropyl, or R and $R_1$ are methyl, or R and $R_1$ are taken together with the carbon atom to which they are attached to form a cyclopropyl group;

Ar is phenyl optionally substituted with up to three groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups;

$Ar_1$ is 3-phenoxyphenyl optionally substituted with up to five groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups, 3-biphenyl optionally substituted with up to five groups independently selected from halogen atoms, $C_1-C_4$alkyl groups, $C_1-C_4$haloalkyl groups, $C_1-C_4$alkoxy groups or $C_1-C_4$haloalkoxy groups, 3-benzylphenyl optionally substituted with up to five groups independently selected from halogen atoms, $C_1-C_4$alkyl groups, $C_1-C_4$haloalkyl groups, $C_1-C_4$alkoxy groups or $C_1-C_4$haloalkoxy groups, or 3-benzoylphenyl optionally substituted with up to five groups independently selected from halogen atoms, $C_1-C_4$alkyl groups, $C_1-C_4$haloalkyl groups, $C_1-C_4$alkoxy groups or $C_1-C_4$haloalkoxy groups; and $R_2$ is $C_1-C_4$alkyl.

8. The process according to claim 7 wherein Ar is 4-chlorophenyl, 4-fluorophenyl, 4-(trifluoromethoxy) phenyl or 4-ethoxyphenyl; and $Ar_1$ is 4-fluoro-3-phenoxyphenyl or 3-phenoxyphenyl.

9. A process according to claim 7 wherein:

the second base is a tertiary amine selected from the group consisting of a tri($C_1-C_4$alkyl)amine, pyridine and a substituted pyridine;

said fluorinating step comprises reacting the formula II compound with at least about one molar equivalent of a fluorinating agent selected from the group consisting of fluorine, diethylaminosulfur trifluoride, 1-fluoro-4-hydroxy-1,4-diazoniabicyclo[2.2.2]octane bis (tetrafluoroborate), N-fluoropyridinium pyridine heptafluorodiborate, N-fluorobenzenesulfonimide, N-fluoro-3,3-dimethyl-2,3-dihydro-1,2-benzothiazol-1,1-dioxide and an N-fluoro oxathiazinone dioxide, in the presence of at least about one molar equivalent of the first base, which is selected from the group consisting of an alkali metal hydroxide, an alkaline earth metal hydroxide, an alkali metal $C_1-C_6$alkoxide, an alkaline earth metal $C_1-C_6$alkoxide, a thallium(I) $C_1-C_6$alkoxide, thallium(I) hydroxide, an alkali metal hydride, an alkyl lithium and an aryl lithium, in the presence of a first solvent, at a temperature in the approximate range of −15° C. to 100° C.;

said reducing step comprises reacting the formula III compound with at least one molar equivalent of a reducing agent selected from the group consisting of a borohydride, a substituted aluminum hydride, an aluminum $C_1-C_6$alkoxide/$C_1-C_6$alcohol complex, and hydrogen in the presence of a noble metal catalyst, at a temperature in the approximate range of −50° C. to 80° C., in the presence of a second solvent;

said saponifying step comprises reacting the formula IV compound with at least about one molar equivalent of a base selected from the group consisting of an alkali metal carbonate, an alkaline earth metal carbonate, an alkali metal hydroxide, an alkaline earth metal hydroxide, an alkali metal $C_1-C_6$alkoxide, an alkaline earth metal $C_1-C_6$alkoxide, thallium(I) carbonate, a thallium(I) $C_1-C_6$alkoxide and thallium(I) hydroxide, followed by at least about one molar equivalent of an acid, at a temperature in the approximate range of −15° C. to 80° C., in the presence of a third solvent; and said reaction with the sulfonyl halide compound includes at least about one molar equivalent of a sulfonyl halide compound selected from the group consisting of an alkylsulfonyl chloride and an arylsulfonyl chloride, and at least one m,olar equivalent of a second base acid, at a temperature in the approximate range of 0° C. to 130° C., in the preseence of a fourth solvent.

10. A process for the preparation of a fluoroolefin compound having the structural formula I

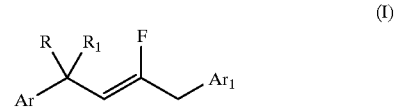

(I)

wherein

R is hydrogen or $C_1-C_4$alkyl, and $R_1$ is $C_1-C_4$alkyl, $C_1-C_4$haloalkyl or cyclopropyl, or R and $R_1$ are taken together with the carbon atom to which they are attached to form a cyclopropyl group;

Ar is phenyl optionally substituted with up to five groups independently selected from halogen atoms, $C_1-C_4$alkyl groups, $C_1-C_4$haloalkyl groups, $C_1-C_4$alkoxy groups or $C_1-C_4$haloalkoxy groups, or 1- or 2-naphthyl optionally substituted with up to three groups independently selected from halogen atoms, $C_1-C_4$alkyl groups, $C_1-C_4$haloalkyl groups, $C_1-C_4$alkoxy groups or $C_1-C_4$haloalkoxy groups;

$Ar_1$ is phenoxyphenyl optionally substituted with up to five groups independently selected from halogen atoms, $C_1-C_4$alkyl groups, $C_1-C_4$haloalkyl groups, $C_1-C_4$alkoxy groups or $C_1-C_4$haloalkoxy groups, biphenyl optionally substituted with up to five groups independently selected from halogen atoms, $C_1-C_4$alkyl groups, $C_1-C_4$haloalkyl groups, $C_1-C_4$alkoxy groups or $C_1-C_4$haloalkoxy groups, benzylphenyl optionally substituted with up to five groups independently selected from halogen atoms, $C_1-C_4$alkyl groups, $C_1-C_4$haloalkyl groups, $C_1-C_4$alkoxy groups or $C_1-C_4$haloalkoxy groups, or benzoylphenyl optionally substituted with up to five groups independently selected from halogen atoms, $C_1-C_4$alkyl groups, $C_1-C_4$haloalkyl groups, $C_1-C_4$alkoxy groups or $C_1-C_4$haloalkoxy groups; and the configuration of the groups $ArCRR_1$— and —$CH_2Ar_1$ about the double bond is predominantly mutually trans, which process comprises reacting a 4-aryl-2-fluoro-3-hydroxy-2-(substituted benzyl)butanoic acid compound having the structural formula V

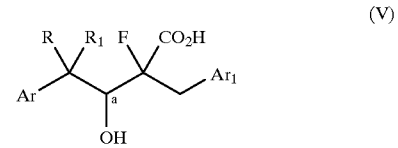

(V)

wherein Ar, $Ar_1$, R and $R_1$ are as described above and the configuration of the groups $ArCRR_1CH(OH)$— and —$CF(CO_2H)CH_2Ar_1$ attached to the bond labelled "a" is predominantly R,S or S,R or a mixture thereof with a sulfonyl halide compound and a base.

11. The process according to claim 10 wherein the sulfonyl halide compound is selected from the group consisting of a alkylsulfonyl chloride and an arylsulfonyl chloride, and the base is a tertiary amine.

12. The process according to claim 10 wherein

R is hydrogen and $R_1$ is isopropyl or cyclopropyl, or R and $R_1$ are methyl, or R and $R_1$ are taken together with the carbon atom to which they are attached to form a cyclopropyl group;

Ar is phenyl optionally substituted with up to three groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups; and $Ar_1$ is 3-phenoxyphenyl optionally substituted with up to five groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups, 3-biphenyl optionally substituted with up to five groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups, 3-benzylphenyl optionally substituted with up to five groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups, or 3-benzoylphenyl optionally substituted with up to five groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups.

13. The process according to claim 12 wherein

Ar is 4-chlorophenyl 4-fluorophenyl, 4-(trifluoromethoxy)phenyl or 4-ethoxyphenyl; and $Ar_1$ is 4-fluoro-3-phenoxyphenyl or 3-phenoxyphenyl.

14. A process for the preparation of a fluoroolefin compound having the structural formula I

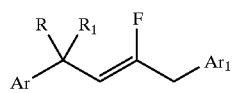

(I)

wherein

R is hydrogen or $C_1$–$C_4$alkyl, and $R_1$ is $C_1$–$C_4$alkyl, $C_1$–$C_4$haloalkyl or cyclopropyl, or R and $R_1$ are taken together with the carbon atom to which they are attached to form a cyclopropyl group;

Ar is phenyl optionally substituted with up to three groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups, or 1- or 2-naphthyl optionally substituted with up to three groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups;

$Ar_1$ is phenoxyphenyl optionally substituted with up to five groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups, biphenyl optionally substituted with up to five groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups, benzylphenyl optionally substituted with up to five groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups, or benzoylphenyl optionally substituted with up to five groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups; and the configuration of the groups $ArCRR_1$— and —$CH_2Ar_1$ about the double bond is predominantly mutually trans, which process comprises a) reducing a 4-aryl-2-fluoro-3-oxo-2-(substituted benzyl)butanoate compound having the structural formula III

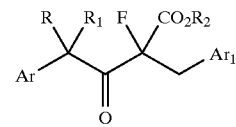

(III)

wherein $R_2$ is $C_1$–$C_6$alkyl and Ar, $Ar_1$, R and $R_1$ are as described above to form a 4-aryl-2-fluoro-3-hydroxy-2-(substituted benzyl)butanoate compound having the structural formula IV

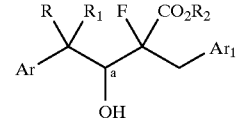

(IV)

wherein Ar, $Ar_1$, R, $R_1$ and $R_2$ are as described above and the configuration of the groups $ArCRR_1CH(OH)$— and —$CF(CO_2R_2)CH_2Ar_1$ attached to the bond labelled "a" is predominantly R,S or S,R or a mixture thereof;

b) saponifying the formula IV compound to form a 4-aryl-2-fluoro-3-hydroxy-2-(substituted benzyl)butanoic acid compound having the structural formula V

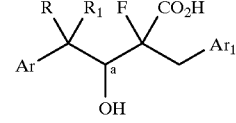

(V)

wherein Ar, $Ar_1$, R and $R_1$ are as described above and the configuration of the groups $ArCRR_1CH(OH)$— and —$CF(CO_2H)CH_2Ar_1$ attached to the bond labelled "a" is predominantly R,S or S,R or a mixture thereof; and c) reacting the formula V compound with a sulfonyl halide compound and a base.

15. The process according to claim 14 wherein: said reducing step comprises reacting the formula III compound with a reducing agent selected from the group consisting of a borohydride, a substituted aluminum hydride, an aluminum $C_1$–$C_6$alkoxide/$C_1$–$C_6$alcohol complex and hydrogen in the presence of a noble metal catalyst; said saponifying step comprises reacting the formula IV compound with a base selected from the group consisting of an alkali metal carbonate, an alkaline earth metal carbonate, an alkali metal hydroxide, an alkaline earth metal hydroxide, an alkali metal $C_1$–$C_6$alkoxide, an alkaline earth metal $C_1$–$C_6$alkoxide, thallium(I) carbonate, a thallium(I) $C_1$–$C_6$alkoxide and thallium(I) hydroxide; the sulfonyl halide compound is selected from the group consisting of an alkylsulfonyl chloride and an arylsulfonyl chloride; and the base is a tertiary amine.

16. The process according to claim 14 wherein

R is hydrogen and $R_1$ is isopropyl or cyclopropyl, or R and $R_1$ are methyl, or R and $R_1$ are taken together with the carbon atom to which they are attached to form a cyclopropyl group;

Ar is phenyl optionally substituted with up to three groups independently selected from halogen atoms, $C_1$–$C_4$ alkyl groups, $C_1$–$C_4$ haloalkyl groups, $C_1$–$C_4$ alkoxy groups or $C_1$–$C_4$ haloalkoxy groups;

$Ar_1$ is 3-phenoxyphenyl optionally substituted with up to five groups independently selected from halogen atoms, $C_1$–$C_4$ alkyl groups, $C_1$–$C_4$ haloalkyl groups, $C_1$–$C_4$ alkoxy groups or $C_1$–$C_4$ haloalkoxy groups, 3-biphenyl optionally substituted with up to five groups independently selected from halogen atoms, $C_1$–$C_4$ alkyl groups, $C_1$–$C_4$ haloalkyl groups, $C_1$–$C_4$ alkoxy groups or $C_1$–$C_4$ haloalkoxy groups, 3-benzylphenyl optionally substituted with up to five groups independently selected from halogen atoms, $C_1$–$C_4$ alkyl groups, $C_1$–$C_4$ haloalkyl groups, $C_1$–$C_4$ alkoxy groups or $C_1$–$C_4$ haloalkoxy groups, or 3-benzoylphenyl optionally substituted with up to five groups independently selected from halogen atoms, $C_1$–$C_4$ alkyl groups, $C_1$–$C_4$ haloalkyl groups, $C_1$–$C_4$ alkoxy groups or $C_1$–$C_4$ haloalkoxy groups; and $R_2$ is $C_1$–$C_4$ alkyl.

17. The process according to claim 16 wherein
Ar is 4-chlorophenyl, 4-fluorophenyl, 4-(trifluoromethoxy)phenyl or 4-ethoxyphenyl; and
$Ar_1$ is 4-fluoro-3-phenoxyphenyl or 3-phenoxyphenyl.

18. A compound having the structural formula

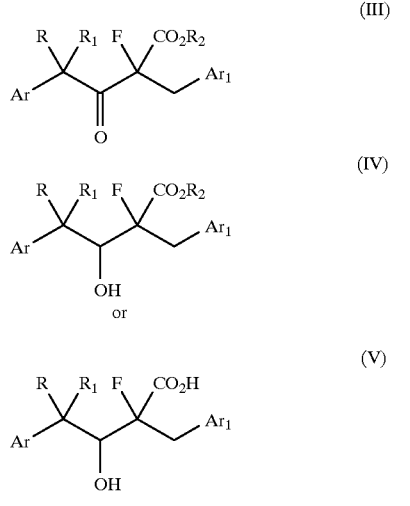

wherein
R is hydrogen or $C_1$–$C_4$ alkyl, and
$R_1$ is $C_1$–$C_4$ alkyl, $C_1$–$C_4$ haloalkyl or cyclopropyl, or R and $R_1$ are taken together with the carbon atom to which they are attached to form a cyclopropyl group;
Ar is phenyl optionally substituted with up to three groups independently selected from halogen atoms, $C_1$–$C_4$ alkyl groups, $C_1$–$C_4$ haloalkyl groups, $C_1$–$C_4$ alkoxy groups or $C_1$–$C_4$ haloalkoxy groups, or
1- or 2-naphthyl optionally substituted with up to three groups independently selected from halogen atoms, $C_1$–$C_4$ alkyl groups, $C_1$–$C_4$ haloalkyl groups, $C_1$–$C_4$ alkoxy groups or $C_1$–$C_4$ haloalkoxy groups;
$Ar_1$ is phenoxyphenyl optionally substituted with up to five groups independently selected from halogen atoms, $C_1$–$C_4$ alkyl groups, $C_1$–$C_4$ haloalkyl groups, $C_1$–$C_4$ alkoxy groups or $C_1$–$C_4$ haloalkoxy groups,
biphenyl optionally substituted with up to five groups independently selected from halogen atoms, $C_1$–$C_4$ alkyl groups, $C_1$–$C_4$ haloalkyl groups, $C_1$–$C_4$ alkoxy groups or $C_1$–$C_4$ haloalkoxy groups,
benzylphenyl optionally substituted with up to five groups independently selected from halogen atoms, $C_1$–$C_4$ alkyl groups, $C_1$–$C_4$ haloalkyl groups, $C_1$–$C_4$ alkoxy groups or $C_1$–$C_4$ haloalkoxy groups, or
benzoylphenyl optionally substituted with up to five groups independently selected from halogen atoms, $C_1$–$C_4$ alkyl groups, $C_1$–$C_4$ haloalkyl groups, $C_1$–$C_4$ alkoxy groups or $C_1$–$C_4$ haloalkoxy groups; and $R_2$ is $C_1$–$C_6$ alkyl; and
the optical isomers and diastereomers thereof.

19. The compound according to claim 18 wherein
R is hydrogen and $R_1$ is isopropyl or cyclopropyl, or R and $R_1$ are methyl, or R and $R_1$ are taken together with the carbon atom to which they are attached to form a cyclopropyl group;
Ar is phenyl optionally substituted with up to three groups independently selected from halogen atoms, $C_1$–$C_4$ alkyl groups, $C_1$–$C_4$ haloalkyl groups, $C_1$–$C_4$ alkoxy groups or $C_1$–$C_4$ haloalkoxy groups;
$Ar_1$ is 3-phenoxyphenyl optionally substituted with up to five groups independently selected from halogen atoms, $C_1$–$C_4$ alkyl groups, $C_1$–$C_4$ haloalkyl groups, $C_1$–$C_4$ alkoxy groups or $C_1$–$C_4$ haloalkoxy groups, 3-biphenyl optionally substituted with up to five groups independently selected from halogen atoms, $C_1$–$C_4$ alkyl groups, $C_1$–$C_4$ haloalkyl groups, $C_1$–$C_4$ alkoxy groups or $C_1$–$C_4$ haloalkoxy groups, 3-benzylphenyl optionally substituted with up to five groups independently selected from halogen atoms, $C_1$–$C_4$ alkyl groups, $C_1$–$C_4$ haloalkyl groups, $C_1$–$C_4$ alkoxy groups or $C_1$–$C_4$ haloalkoxy groups, or 3-benzoylphenyl optionally substituted with up to five groups independently selected from halogen atoms, $C_1$–$C_4$ alkyl groups, Cl-$C_4$ haloalkyl groups, $C_1$–$C_4$ alkoxy groups or $C_1$–$C_4$ haloalkoxy groups; and $R_2$ is $C_1$–$C_4$ alkyl.

20. The compound according to claim 19 wherein
Ar is 4-chlorophenyl, 4-fluorophenyl, 4-(trifluoromethoxy)phenyl or 4-ethoxyphenyl; and
$Ar_1$ is 4-fluoro-3-phenoxyphenyl or 3-phenoxyphenyl.

21. A compound having the structural formula II

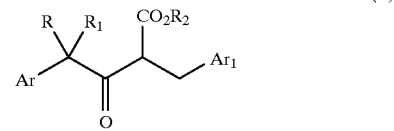

wherein
R is $C_1$–$C_4$ alkyl, and
$R_1$ is $C_1$–$C_4$ alkyl, $C_1$–$C_4$ haloalkyl or cyclopropyl, or R and $R_1$ are taken together with the carbon atom to which they are attached to form a cyclopropyl group;
Ar is phenyl optionally substituted with up to three groups independently selected from halogen atoms, $C_1$–$C_4$ alkyl groups, $C_1$–$C_4$ haloalkyl groups, $C_1$–$C_4$ alkoxy groups or $C_1$–$C_4$ haloalkoxy groups, or
1- or 2-naphthyl optionally substituted with up to three groups independently selected from halogen atoms, $C_1$–$C_4$ alkyl groups, $C_1$–$C_4$ haloalkyl groups, $C_1$–$C_4$ alkoxy groups or $C_1$–$C_4$ haloalkoxy groups;
$Ar_1$ is phenoxyphenyl optionally substituted with up to five groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups, biphenyl optionally substituted with up to five groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups, benzylphenyl optionally substituted with up to five groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups, or benzoylphenyl optionally substituted with up to five groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups; and $R_2$ is $C_1$–$C_6$alkyl; and the optical isomers thereof.

22. The compound according to claim 21 wherein

R an $R_1$ are methyl, or R and $R_1$ are taken together with the carbon atom to which they are attached to form a cyclopropyl group;

Ar is phenyl optionally substituted with up to three groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups;

$Ar_1$ is 3-phenoxyphenyl optionally substituted with up to five groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups, 3-biphenyl optionally substituted with up to five groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups, 3-benzylphenyl optionally substituted with up to five groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups, or 3-benzoylphenyl optionally substituted with up to five groups independently selected from halogen atoms, $C_1$–$C_4$alkyl groups, $C_1$–$C_4$haloalkyl groups, $C_1$–$C_4$alkoxy groups or $C_1$–$C_4$haloalkoxy groups; and $R_2$ is $C_1$–$C_4$alkyl.

23. The compound according to claim 22 wherein

Ar is 4-chlorophenyl, 4-fluorophenyl, 4-(trifluoromethoxy)phenyl or 4-ethoxyphenyl; and $Ar_1$ is 4-fluoro-3-phenoxyphenyl or 3-phenoxyphenyl.

* * * * *